United States Patent [19]

Yoshida et al.

[11] Patent Number: 5,256,569

[45] Date of Patent: Oct. 26, 1993

[54] TRANSESTERIFICATION PROCESS FOR OTEREOSELECTION OF ENANTIOMERS OF SECONDARY ALCOHOLS USING PSEUDOMONAS LIPASE WITH NO ADDED SOLVENT

[75] Inventors: Naoyuki Yoshida, Kamakura; Hiroshi Morita, Yokohama, both of Japan

[73] Assignee: Chisso Corporation, Osaka, Japan

[21] Appl. No.: 931,418

[22] Filed: Aug. 24, 1992

Related U.S. Application Data

[63] Continuation of Ser. No. 609,108, Nov. 2, 1990, abandoned, which is a continuation of Ser. No. 517,531, May 1, 1990, abandoned, which is a continuation of Ser. No. 3,284, Jan. 14, 1987, abandoned.

[30] Foreign Application Priority Data

Jan. 21, 1986 [JP] Japan .................................. 61-8997

[51] Int. Cl.$^5$ .......................... C12P 41/00; C12P 7/62
[52] U.S. Cl. .................................. 435/280; 435/135; 435/874
[58] Field of Search ..................... 435/280, 135, 874

[56] References Cited

U.S. PATENT DOCUMENTS

| | | | |
|---|---|---|---|
| 4,472,503 | 9/1984 | Matsuo et al. | 435/198 |
| 4,603,124 | 7/1986 | Takei et al. | 514/78 |
| 4,765,987 | 8/1988 | Bonte et al. | 514/78 |
| 5,032,585 | 7/1991 | Lichtenberger | 514/78 |

OTHER PUBLICATIONS

Kirchner et al, "Resolution of Racemic Mixtures Via Lipase Catalysis in Organic Solvents", J. Am. Chem. Soc. v. 107, 7072–76, 1985.
Cambou et al (A), "Unusual Catalytic Properties of Usual Enzymes", New York Academy of Sciences, v. 434, 219–223, 1984.
Cambou et al (B), "Preparative Production of Optically Active Esters and Alcohols Using Esterase-Catalyzed Stereospecific Transesterification in Organic Media" J. Am. Chem. Soc. v. 106, 2687–2692, 1984.
von Seefeld et al., Fortschr Med 102(39): 977–981 (Oct. 18, 1984).
Schlimmer et al., Eur J. Resp Dis Suppl., 128 (Pt. 1): 318–321 (1983).

*Primary Examiner*—Douglas W. Robinson
*Assistant Examiner*—S. Saucier
*Attorney, Agent, or Firm*—Wenderoth, Lind & Ponack

[57] ABSTRACT

An optically active alcohol of this invention is obtained from a process using an enzyme having the ability to conduct preferentially a transesterification reaction with a triglyceride and an (R,S)-alcohol represented by a general formula:

$$X-\underset{\underset{H}{|}}{\overset{\overset{Y}{|}}{C}}-OH \qquad (1)$$

wherein X indicates alkyl group having a carbon number of 2-10, Y indicates alkyl group having a carbon number of 1-3, $CF_3$ or CN, and $X \neq Y$. In this process, the (R,S)-alcohol of the above formula (1) and the triglyceride are reacted under substantially anhydrous conditions. The obtained ester is resolved and the optically active alcohol which contains richly either R- or S-alcohol is produced the optically active alcohol is efficiently obtained by an industrially advantageous biochemical method.

4 Claims, No Drawings

TRANSESTERIFICATION PROCESS FOR OTEREOSELECTION OF ENANTIOMERS OF SECONDARY ALCOHOLS USING PSEUDOMONAS LIPASE WITH NO ADDED SOLVENT

This application is a continuation of now abandoned application Ser. No. 07/609,108, filed Nov. 2, 1990, which application is a continuation of now abandoned application Ser. No. 517,531, filed May 1, 1990, which application is a continuation of now abandoned application Ser. No. 07/003,284, filed Jan. 14, 1987.

BACKGROUND OF THE INVENTION

1. Fields of the Invention

This invention relates to a process for producing optically active alcohols by a biochemical method in which secondary alcohols are reacted with triglycerides in the presence of enzymes.

2. Description of the Prior Art

Optically active alcohols are known as chemical compounds which have a great demand as physiologically active substances, such as medical supplies, agricultural chemicals and so on, or as intermediates.

However, secondary alcohols represented by the formula:

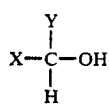

wherein X indicates an alkyl group having a carbon number of 2-10, Y indicates an alkyl group having a carbon number of 1-3, $CF_3$ or CN, and $X \neq Y$, have optical isomers, so that these alcohols do not sufficiently exhibit activity in many cases unless either the R- or S-alcohol is in pure form.

For the above reason, in order to obtain optically active substances, it is necessary to optically resolve racemates which are obtained by a common method of synthetic chemical preparation, to conduct asymmetric synthesis or to synthesize in pare form from optically active materials by a stereochemical method.

Accordingly, it is desired to develop a technique for optically resolving the secondary alcohols by an industrially advantageous method.

The known optical resolution method of the secondary alcohols also needs complex steps and an expensive optical activator. For example, the salt is prepared by the steps in which 2-butanol or 2-octanol is reacted with phthalic acid, the obtained alkyl hydrogen phthalate is reacted with brucine, and the corresponding salt is repeatedly crystalized to resolve 2-butanol or 2-octanol. (Ref. Org. Syntheses, Coll. Vol. I, 418, 2nd ed., 1941).

Further, it is known that the optically active substances are obtained by optical resolution by biochemical methods.

For example, a method of Klibanov et al. (J. Am. Chem. Soc., 106, 2687 (1984)) uses yeast lipase or pig liver carboxy esterase dissolved in an aqueous buffered solution. In this case, unnecessary hydrolysis of triglyceride is unavoidable in the presence of moisture. Moreover, the enzyme is soluble in water and is unstable to moisture. In order to use the enzyme in a stable condition, it must be fixed on a polymer. In other words, one is unable to remove or reuse the enzyme unless it is fixed on the polymer.

There are biochemical methods in addition to the above method (Japanese Publication of Unexamined Patent Application No. Sho 59-205989 and others). In any case, one needs to use a buffered solution or lower alcohol, and an enzyme must be fixed on a carrier.

Klibanov et al. also reported a method in which enzyme powder was directly added to a reaction system (J. Am. Chem. Soc., 107, 7072 (1985)). In this case, heptane or ether is used as its solvent, and not triglyceride but monoester is used as an ester.

The present inventors have conducted research for resolving the above problems and for obtaining a process for producing an optically active secondary alcohol by an advantageous industrial method and have found that a racemic secondary alcohol of a raw material is efficiently resolved to an optically active aliphatic ester and its antipode, namely an optically active alcohol, by a biochemical transesterification reaction.

SUMMARY OF THE INVENTION

An object of the invention is to provide a process for producing an optically active alcohol by a biochemical method, in which the alcohol is efficiently obtained by an industrially advantageous method.

Namely, this invention provides a process for producing an optically active alcohol that comprises using an enzyme having the ability to conduct preferentially a transesterification reaction with a triglyceride and an (R,S)-alcohol represented by the general formula:

wherein X indicates an alkyl group having a carbon number of 2-10, Y indicates an alkyl group having a carbon number of 1-3, $CF_3$ or CN, and $X \neq Y$, reacting the (R,S)-alcohol of the above formula (1) and the triglyceride to conduct the transesterification reaction under substantially anhydrous conditions and resolving the resulting ester to obtain an optically active alcohol which contains richly either R- or S-alcohol. The above reaction is represented by the following chemical equation:

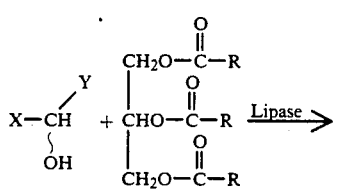

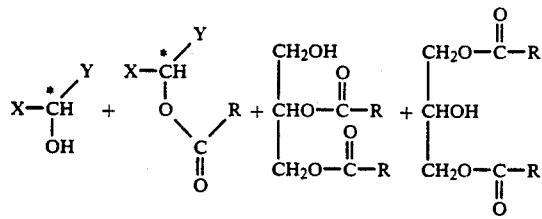

S— and R—
or
R— and S—

According to the method of this invention in comparison with that of the above described Klibanov et al. process, the triglyceride does not hydrolyze because the method does not need the use of a small amount of water or alcohol instead of water, so that the enzyme remain stable in organic solvent and is easily separated after the reaction for reuse. Furthermore, since the method of this invention is kept from free contaminant of microorganism, there is no necessity for preparing special equipments, antiseptics, etc.. It is possible to conduct the reaction in an open system.

The following description illustrates this invention more specifically.

In this invention, the (R,S)-alcohols of the raw materials are compounds which are easily available and can be synthesized without difficulty. It is sufficient to use the compounds which are commercially available such as 2-butanol, 2-pentanol, 2-hexanol, 2-heptanol, 2-octanol, 2-nonanol, 2-decanol etc.. Moreover, a compound of formula (1) in which $Y=CF_3$ can be synthesized by the method of Campbell et al. (J. Am. Chem. Soc., 72, 4380 (1950)). A compound of formula (1) in which $Y=CN$, is easily also obtainable by the reaction of an aldehyde with hydrogen cyanide.

It is also sufficient to use the triglyceride which is commercially available without any difficulty, such as triacetin, tripropyonin, tributyrin, tristearin, trilaurin, trimyristin, triolein etc..

As the enzyme which is used in this invention, a lipase of the pseudomonas genus is preferable in particular. If the enzyme has the ability of performing the transesterification reaction preferentially between either the R- or S- alcohol and triglyceride when the enzyme is reacted with the (R,S)-alcohol, the enzyme can be used regardless of its class. The following table shows commercially available enzymes that can be used in this reaction.

| Trade name | Origin | Seller or Maker |
| --- | --- | --- |
| Lipase AP | Aspergillus niger | Amano Pharmaceutical Co., Ltd |
| Lipase M | Mucor javanicus | Amano Pharmaceutical Co., Ltd |
| Lipase P | Pseudomonas fluorescens | Amano Pharmaceutical Co., Ltd |
| Lipase CES | Pseudomonas sp | Amano Pharmaceutical Co., Ltd |
| Lipase CE | Humicola lanuginosa | Amano Pharmaceutical Co., Ltd |
| Lipase F-AP | Rhizopus javanicus | Amano Pharmaceutical Co., Ltd |
| Lipase II | Porcine Pancreas | Sigma Chemical Co. |
| Lipase VII | Geotrichum Candidum | Sigma Chemical Co. |
| Lipase X | Rhizopus delamar | Sigma Chemical Co. |
| Lipase | Chromobacterium Viscosum | Toyo Jozo Co., Ltd. |
| Palatase A | Aspergillus niger | Novo Industi A/S |
| Lipase | Rhisopus niveus | Nagase Biochemicals, Ltd. |

Microorganism which produce the enzymes having the above ability can be used regardless of their species and genus. These micro-organisms are Arthrobactor genus, Acromobacter genus, Chromobacterium genus, Candida genus, Mucor genus, Pseudomonas genus, Phizopus genus etc..

In the practice of the invention, (R,S)-alcohols and triglycerides can be used without any particular treatments.

The transesterification reaction of an (R,S)-alcohol is conducted by mixing the (R,S)-alcohol with a triglyceride and contacting efficiently the mixture with an enzyme. The reaction temperature is suitably 20°-70° C. and preferably 30°-45° C. The reaction time is broadly 48-1000 hours. Short reaction time depends on elevated reaction temperature, raised activity of the enzyme and lowered concentration of substrates.

The (R,S)-alcohol and the triglyceride which are substrates, are mixed in the ratio of 1:0.5-1:5 by mole and preferably 1:1.2-1:2.

After the transesterification reaction, the enzyme can be removed by common filter operation and used again as it is. The filtrate can be separated into an optically active alcohol and an ester. The obtained ester is commonly hydrolyzed in an alkali solution to derive an optically active alcohol which is an antipode of the above alcohol.

By the above described process, an optically R-and S-alcohol can be obtained.

The effects of this invention are as follows.
(1) Triglyceride is hardly hydrolyzed because it is substantially reacted under the conditions of being water free.
(2) The enzyme can be easily recovered and reused.
(3) No special equipment and materials are used because the reaction can be conducted under the conditions of relatively lower temperatures and an open system.
(4) Optically active substances having high purity are obtained by a one step reaction.

DESCRIPTION OF PREFERRED EMBODIMENTS

The following Examples illustrate this invention more specifically, but these will not always be precise in practical applications.

EXAMPLE 1

10 g of enzyme (produced by Amano pharmaceutical Co. Ltd., lipase "Amano" P), 65.1 g (0.5 mol) of (R, S)-2-octanol and 208.0 g (0.69 mol) of tributyrin were charged into a three-necked flask and reacted with stirring for 36 days at 35° C. After the reaction, (at this point, by detecting the ratio of compounds in the reaction solution with GPC, the ratio was 14.9% of 2-octanol, 27.0% of 2-octylbutyrate 17.8% of dibutyrin and 36.1% of tributyrin) the enzyme was removed by filtration and washed in toluene. The solution was added to the filtrate and then distilled under vacuum.

22.8 g of S-(+)-2-octanol (yield: 70%, >99% ee) was obtained at the boiling point of 78°-82° C./14 mmHg, and 42.9 g of R-(−)-2-octyl butyrate (yield: 73%, 72% ee) was obtained at the boiling point of 112° C./14 mmHg, respectively.

Finally, R-(−)-2-octyl butyrate was hydrolyzed in alkali solution to obtain R-(−)-2-octanol (yield: 98%, 72% ee).

The obtained compounds were identified by structure analysis with NMR and optical activity with a polarimeter. Furthermore, the optical purity was determined by the comparison of the specific optical activity between the obtained compounds and authentic samples.

COMPARISON EXAMPLE 1

Using the same reactor as used in Example 1, the enzyme, 2-octanol and tributyrin were reacted under the same conditions as in Example 1 except that 50 ml of 0.1M-KPB (pH 8.0) was added. After 77 hours, the compounds in the reaction solution were detected with GPC, the ratio was 14.5% of butyric acid, 46.4% of 2-octanol, 4.0% of 2-octyl butyrate, 16.1% of dibutyrin and 15.5% of tributyrin.

The result shows that the hydrolysis of tributyrin is more preferential than the transesterification reaction in the presence of a small amount of water, so that the optical resolution could not be conducted.

EXAMPLE 2

Using the same enzyme as used in Example 1 under the same conditions as in Example 1, 23.4 g of S-(+)-2-octanol (yield: 71%, >99% ee) and 46.2 g of R-(−)-2-octyl butyrate (yield: 92%, 69% ee) were obtained.

Moreover, the above enzyme was used under the same conditions as in Example 1 several times, and its deactivation was hardly found during the reaction.

Then the desired S-(+)-2-octanol and R-(−)-2-octyl butyrate were obtained.

The obtained compounds were identified and determined by the same method as in Example 1.

EXAMPLE 3

40 g of the same enzyme as used in Example 1, 158.3 g (1 mol) of (R,S)-2-decanol and 332.6 g (1.1 mol) of tributyrin were reacted under the same conditions as in Example 1, 64 g of S-(+)-2-decanol (yield: 81%, >78% ee) was obtained at the boiling point of 84° C./4.5 mmHg, and 105 g of R-(−)-2-octyl butyrate (yield: 92%, 71% ee) was obtained at the boiling point of 107° C./3.5 mHg, respectively.

The obtained compounds were identified and determined by the same method as in Example 1.

EXAMPLE 4

Using the same reactor under the same conditions as in Example 1 except that (R,S)-2-octanol was replaced by (R,S)-2-pentanol. S-(+)-2-pentanol (yield: 73.2%, >62% ee) and R-(−)-2-pentyl butyrate (yield: 82.2%) were obtained, respectively.

The obtained compounds were identified and determined by the same method as in Example 1.

EXAMPLE 5

Using the same reactor under the same conditions as in Example 1, except that tributyrin was replaced by tripropionin, S-(+)-2-octanol (yield: 71%, >91% ee) and R-(−)-2-octyl propionate (yield: 86%) were obtained, respectively.

The obtained compounds were identified and determined by the same method as in Example 1.

EXAMPLE 6-8

Using the same method under the same conditions as in Example 1, optically active secondary alcohols having yields as shown in the following table were obtained.

| | | S | | R | |
|---|---|---|---|---|---|
| Example | Alcohol | yield (%) | ee (%) | yield (%) | ee (%) |
| 6 | 2-hexanol | 68 | 93 | 67 | 73 |
| 7 | 2-heptanol | 76 | 86 | 69 | 74 |
| 8 | 2-nonanol | 61 | 89 | 80 | 52 |
| 9 | 3-nonanol | 60 | 88 | 93 | 75 |

We claim:

1. A process for producing an optically active alcohol using a lipase powder from Pseudomonas genus, which consists of mixing (a) an (R,S)-alcohol of the formula:

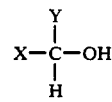

wherein X is an alkyl group of 2-20 carbon atoms, Y is an alkyl group of 1-3 carbon atoms, $CF_3$, or CN, and X and Y are different, with (b) a triglyceride and (c) said lipase powder and allowing said (R,S) alcohol and said triglyceride to react in the presence of the said lipase powder under substantially anhydrous conditions and resolving the resulting mixture to obtain an optically active alcohol or ester which is enriched in either the R-or S-configuration.

2. The process according to claim 1, wherein Y is $CH_3$.

3. The process according to claim 1, wherein Y is $C_2H_5$.

4. The process according to claim 1, wherein Y is $CF_3$.

UNITED STATES PATENT AND TRADEMARK OFFICE
CERTIFICATE OF CORRECTION

PATENT NO. : 5,256,569

DATED : October 26, 1993

INVENTOR(S) : NAOYUKI YOSHIDA and HIROSHI MORITA

It is certified that error appears in the above-identified patent and that said Letters Patent is hereby corrected as shown below:

Item [54], and col. 1, line 2:
On the cover page of the patent, in the title, change "OTEREOSELECTION" to --STEREOSELECTION--

Signed and Sealed this

Seventh Day of June, 1994

Attest:

BRUCE LEHMAN

Attesting Officer

Commissioner of Patents and Trademarks